(12) United States Patent
Haener et al.

(10) Patent No.: US 7,671,184 B2
(45) Date of Patent: Mar. 2, 2010

(54) MOLECULAR BEACONS

(75) Inventors: Robert Haener, Uettingen (CH); Simon Langenegger, Zielebach (CH)

(73) Assignee: Universitact Bern (CH)

( * ) Notice: Subject to any disclaimer, the term of this patent is extended or adjusted under 35 U.S.C. 154(b) by 0 days.

(21) Appl. No.: 11/575,875

(22) PCT Filed: Sep. 22, 2005

(86) PCT No.: PCT/EP2005/010230

§ 371 (c)(1),
(2), (4) Date: Mar. 23, 2007

(87) PCT Pub. No.: WO2006/032487

PCT Pub. Date: Mar. 30, 2006

(65) Prior Publication Data

US 2008/0064033 A1     Mar. 13, 2008

(30) Foreign Application Priority Data

Sep. 24, 2004   (EP)  ................... 04405608

(51) Int. Cl.
*C07H 21/02* (2006.01)
*C07H 21/04* (2006.01)
*C12Q 1/68* (2006.01)
*B01L 3/00* (2006.01)
*C07H 21/00* (2006.01)

(52) U.S. Cl. ................... 536/23.1; 536/24.3; 536/24.33; 536/25.3; 435/6; 422/61

(58) Field of Classification Search ............ 435/6; 536/23.1, 24.3, 24.33, 25.3; 422/61
See application file for complete search history.

(56) References Cited

U.S. PATENT DOCUMENTS

2006/0014144 A1 *   1/2006   Christensen et al. .......... 435/6

FOREIGN PATENT DOCUMENTS

| WO | 03/051901 A2 | 12/2002 |
| WO | 03/052133 A2 | 12/2002 |
| WO | 03/052134 A2 | 12/2002 |
| WO | 03/052132 A2 | 6/2003 |

OTHER PUBLICATIONS

Stratagene catalog p. 39 1988.*

(Continued)

*Primary Examiner*—Jezia Riley
(74) *Attorney, Agent, or Firm*—Joyce von Natzmer; Pequignot + Myers LLC

(57) ABSTRACT

The invention relates to a molecular beacon in the form of a hairpin oligonucleotide or oligonucleotide analogue comprising a first nucleotide sequence containing two or more aromatic or heteroaromatic ring systems P able to form an excimer or exciplex; a second sequence (the loop) consisting of an oligonucleotide probe able to hybridise with a target polynucleotide; and a third sequence containing one or more aromatic or heteroaromatic ring systems X, wherein at least one aromatic ring system X interacts with two aromatic ring systems P of the first sequence inhibiting excimer or exciplex formation. The invention further relates to a method for detecting the presence of a target polynucleotide using such a molecular beacon, and to a kit comprising a molecular beacon of the invention for use in this method.

18 Claims, 4 Drawing Sheets

OTHER PUBLICATIONS

Tyagi, S. et al.:"Molecular Beacons: Probes that fluoresce upon Hybridization", Nature Biotechnology, Nature Publishing Group, New York, NY, US, vol. 14, No. 1, Mar. 1, 1996, pp. 303-308.

Langenegger, S. M. et al.:"The Effect of a Non-Nucleosidic Phenanthrene Building Block on DNA Duplex Stability", Helvetica Chimica Acta, Department of Chemistry and Biochemistry, University of Bern, 2002, vol. 85, pp. 3414-3421.

* cited by examiner

MOLECULAR BEACONS

CROSS-REFERENCE TO RELATED APPLICATIONS

This is the U.S. national stage of International application PCT/EP2005/010230, filed September 22, 2005 designating the United States.

FIELD OF THE INVENTION

The present invention relates to the use of non-nucleosidic, non-hydrogen bonding and interstrand-stacking building blocks in the stem region of a molecular beacon (hairpin oligonucleotide).

BACKGROUND OF THE INVENTION

Molecular beacons are single-stranded oligonucleotide hybridisation probes that form a stem-and-loop structure. The loop contains a probe sequence that is complementary to a target sequence, and the stem is formed by the annealing of complementary sequences located on either side of the probe sequence. A fluorophore is covalently linked to the end of one arm and a quencher to the end of the other arm. In the absence of targets, the probe does not fluoresce, because the stem places the fluorophore so close to the non-fluorescent quencher that they transiently share electrons, eliminating the ability of the fluorophore to fluoresce. When the probe encounters a target molecule, it forms a probe-target hybrid that is longer and more stable than the stem hybrid. The rigidity and length of the probe-target hybrid precludes the simultaneous existence of the stem hybrid. Consequently, the molecular beacon undergoes a conformational reorganization that forces the stem hybrid to dissociate and the fluorophore and the quencher to move away from each other (FIG. 1). For a general overview on the scientific and patent literature of molecular beacons, see Tyagi, S.; Kramer, F. R., *Nature Biotechnology* 1996, 14, 303-308, and www.molecular-beacons.org, a website of Public Health Research Institute, Newark (N.J.), USA.

Molecular beacons can be used as amplicon detector probes in diagnostic assays. Because non-hybridised molecular beacons are non-fluorescent, it is not necessary to isolate the probe-target hybrids to determine the number of amplicons synthesized during an assay. Molecular beacons are added to the assay mixture before carrying out gene amplification and fluorescence is measured in real time. Furthermore, the use of molecular beacons provides an additional level of specificity. Because it is very unlikely that false amplicons or primer-dimers possess target sequences for the molecular beacons, the generation of fluorescence is exclusively due to the synthesis of the intended amplicons.

Molecular beacons with differently coloured fluorophores can be synthesized. This enables assays that simultaneously detect different targets in the same reaction. For example, multiplex assays contain a number of different primer sets, each set enabling the amplification of a unique gene sequence, e.g. from different pathogenic agents. A corresponding number of molecular beacons can be present, each containing a probe sequence specific for one of the amplicons, and each labelled with a fluorophore of a different colour. The colour of the resulting fluorescence identifies the pathogenic agent in the sample and the number of amplification cycles required to generate detectable fluorescence provides a quantitative measure of the number of target sequences present. Moreover, due to the inherent design of gene amplification assays, the use of molecular beacons enables the detection of a rare pathogen in the presence of a much more abundant pathogen.

The stem region of a molecular beacon is particularly critical to the successful application of a molecular beacon. The nucleobases of the stem can interact (or pair) with the nucleic acid target in an undesirable way. This property leads to hybridisation to wrong nucleotide sequences and thus reduces the specificity of the method.

In patent applications WO03/051901, WO03/052132, WO03052133 and WO03052134 (Unest A/S, Christensen, U. B., and Pedersen, E. B.) the use of polyaromatic or heteroaromatic building blocks in oligonucleotides are described. Hairpin oligonucleotides comprising such building blocks are described and claimed, but the authors did not describe the potential of using such building blocks in molecular beacons for stabilizing the stem region as is described in the present invention.

The principle of detecting a target polynucleotide using an oligonucleotide probe comprising substituents able to form an excimer under particular conditions is, for example, described in U.S. Pat. No. 5,332,659 (Kidwell, D. A.). U.S. Pat. No. 5,925,517 (Tyagi, S. et al.) and related patents U.S. Pat. No. 6,103,476; U.S. Pat. No. 6,150,097; and U.S. Pat. No. 6,037,130 describe hybridisation probes with label pairs that can be used to generate a signal when the labels are in close proximity, e.g. FRET pairs consisting of a fluorescent label and a quencher label.

SUMMARY OF THE INVENTION

The invention relates to a molecular beacon in the form of a hairpin oligonucleotide or oligonucleotide analogue comprising a first sequence consisting of n nucleotides and/or nucleotide analogues and two or more aromatic or heteroaromatic ring systems P linked to the oligonucleotide backbone and able to form an excimer or exciplex; a second sequence consisting of an oligonucleotide probe able to hybridise with a target polynucleotide; and a third sequence consisting of m nucleotides and/or nucleotide analogues and one or more aromatic or heteroaromatic ring systems X linked to the oligonucleotide backbone, wherein at least one aromatic or heteroaromatic ring system X interacts with two aromatic or heteroaromatic ring systems P of the first sequence inhibiting excimer or exciplex formation.

The invention further relates to a method for detecting the presence of a target polynucleotide comprising a specified nucleotide sequence, characterized in that the molecular beacon of the invention wherein the second sequence is able to hybridise to said specified nucleotide sequence is added to the target polynucleotide and the change in the fluorescence intensity is measured, and wherein an increase in fluorescence intensity due to excimer or exciplex formation is indicative of the presence of the target polynucleotide. The invention also relates to a kit comprising a molecular beacon of the invention for use in this method.

BRIEF DESCRIPTION OF THE FIGURES

M=molecular beacon, H=hybrid, S=stem, L=loop (complementary to target), T=target, F=fluorophore, Q=quencher

=stem, L=loop (complementary to target), T=target, E=excimer, N=natural nucleotide, Py=pyrene, X=polyaromatic or heteroaromatic hydrocarbon.

Figure 3:
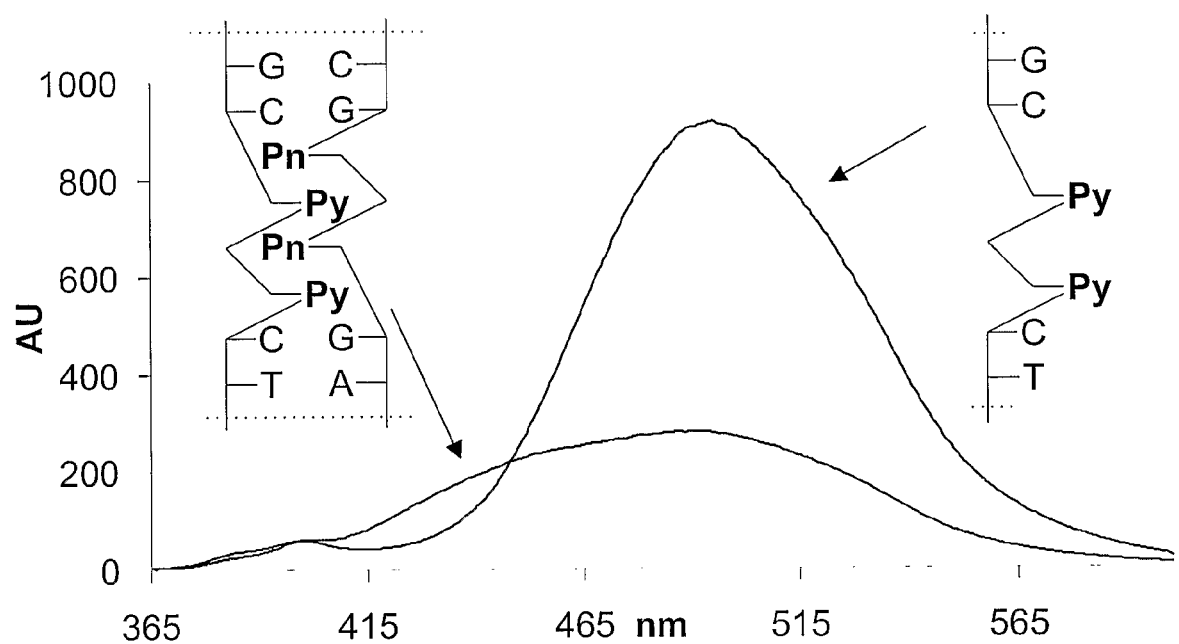

FIG. 3: Fluorescence spectra of the modified duplex and the modified single strand.

Conditions: oligomer concentration 1.0 µM, 10 mM Tris-HCl, 100 mM NaCl, pH 7.4, room temperature. Excitation wavelength: 354 nm; excitation slit: 5 nm; emission slit: 7 nm. AU=fluorescence arbitrary units; Pn=phenanthrene, Py=pyrene.

Figure 4:
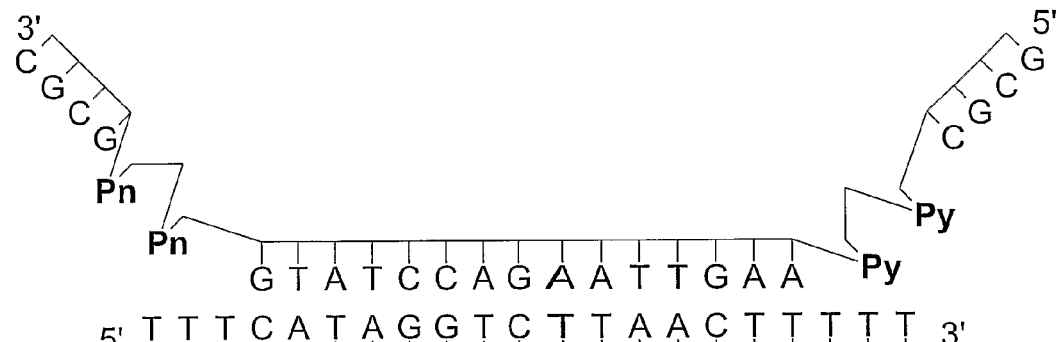
Figure 4:
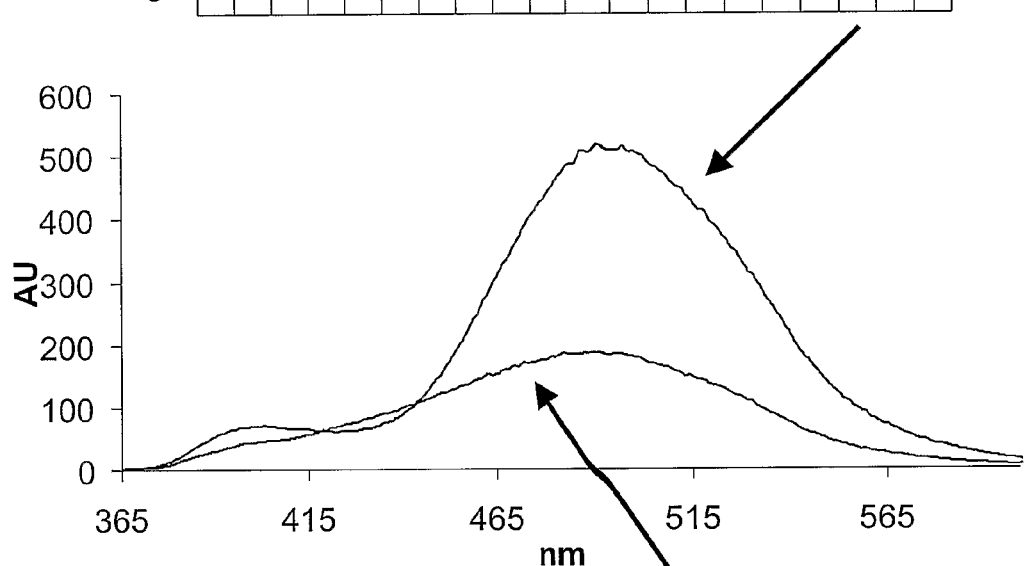
Figure 4:
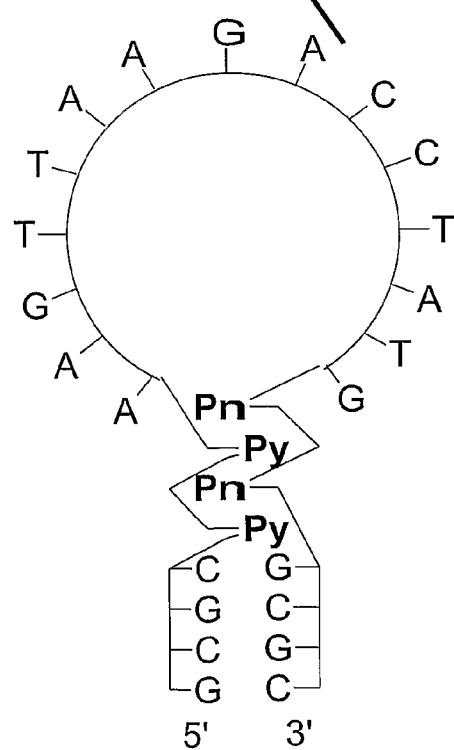

FIG. 4: Fluorescence spectra of Molecular Beacon 1 containing 4 natural nucleoside pairs in the stem, with and without target polynucleotide.

Conditions: molecular beacon concentration 1.0 µM, target polynucleotide concentration 5.0 µM, 100 mM Tris-HCl, 2 mM MgCl$_2$, pH 7.4, room temperature. Excitation wavelength: 354 nm; excitation slit: 5 nm; emission slit: 7 nm. x-axis: wavelength (nm), y-axis fluorescence arbitrary units (AU); Pn=phenanthrene, Py=pyrene.

Figure 5:
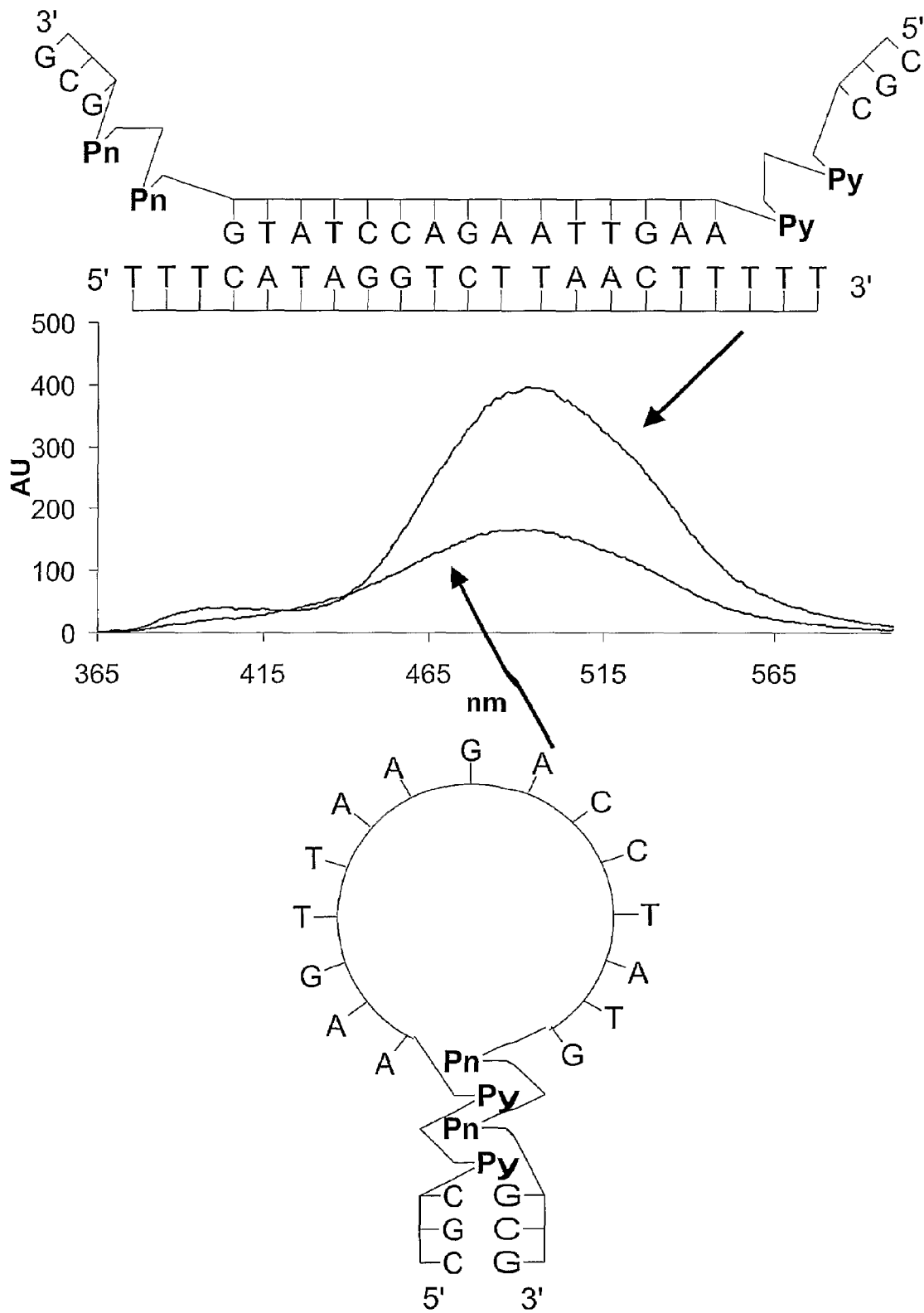

FIG. 5: Fluorescence spectra of Molecular Beacon 2 containing 3 natural nucleoside pairs in the stem, with and without target polynucleotide; Pn=phenanthrene, Py=pyrene. Same conditions as for FIG. 4.

DETAILED DESCRIPTION OF THE INVENTION

The invention relates to a molecular beacon wherein a "first sequence" and a "third sequence" form the stem of a hairpin oligonucleotide, and a "second sequence" connecting the "first sequence" to the "third sequence" represents the loop able to hybridise to a specific sequence within a target polynucleotide. The "first sequence" and the "third sequence" representing the stem comprise building blocks P and X, respectively, which are capable of forming a duplex (just like a nucleic acid) but do not hybridise (pair) with the natural bases of desoxyribonucleic acid (DNA) or ribonucleic acid (RNA). These building blocks P and X interact without hydrogen bonding and provide interstrand stacking due to a flat extended aromatic or heteroaromatic system.

The term "nucleotide analogue" as used in the context of this invention comprises all nucleotide analogues capable of being incorporated into a nucleic acid backbone and capable of specific base-pairing comparable to base-pairing of naturally occurring nucleotides. Such nucleotide analogues are, for example, PNA, HNA, LNA, TNA, homo-DNA, β-D-altropyranosyl nucleic acid, β-D-glucopyranosyl nucleic acid, β-D-allopyranosyl nucleic acid, RNA, 2'-OR-RNA, 2'-lyxopyranosyl nucleic acid, tricyclo-DNA, bicyclo-DNA, and further derivatives of the mentioned analogues.

Building blocks P and X are (poly)aromatic or heteroaromatic hydrocarbons, such as phenanthrene, phenanthroline, naphthalene, anthracene, tetracene, tetraphene, benzo[c]phenanthrene, triphenylene, chrysene, perylene, acenaphthene, biphenyl, fluorene, indole, acridine, phenazine, chinoline, bipyridine, phenanthridine, thianthrene, anthraquinone, phenoxathiine, fluorescein, flavine, coumarine, psoralen, purine, pyrimidine and derivatives thereof, and similar compounds, further bearing one or two linkers, which allow the incorporation into the backbone of an oligonucleotide.

Derivatives of such aromatic or heteroaromatic hydrocarbons are, for example, those carrying (further) substituents selected from alkyl, alkenyl, alkinyl, hydroxy, alkoxy, amino, carboxy, alkoxycarbonyl, carbamoyl, halogen, cyano, thio, alkylthio, sulfonyl, or nitro.

Similar compounds are, for example, compounds which contain a similar extended π system as the compounds listed, such as aromatic or heteroaromatic systems containing phenyl or styryl extensions or related heteroaromatic extensions.

A preferred building block P is pyrene. Preferred building blocks X are phenanthrene and phenanthroline.

Building blocks P within the "first sequence" are further characterized in that two same or different residues P form a fluorescence excimer or exciplex. In an excimer the two identical compounds are associated in an electronic excited state, and an energy transfer takes place. An excimer emits fluorescence at a wavelength different from monomer fluorescence emission. An exciplex is an excimer, wherein the two compounds are different.

Such pairs of building blocks P are, for example, two identical or non-identical members of the following group: pyrene, phenanthroline, naphthalene, anthracene, tetracene, tetraphene, benzo[c]phenanthrene, triphenylene, perylene, and acenaphthene. These pairs of excimer or exciplex-forming building blocks P have to be in neighbouring positions of the "first sequence" oligonucleotide backbone. A preferred pair of building blocks P is pyrene/pyrene.

Building blocks X within the "third sequence" are further characterized in that, on formation of a duplex with the "first sequence" containing a corresponding building block P, they break up an excimer or exciplex formed from a pair of same or different P within the "first sequence". For example, if P is pyrene, X as phenanthrene breaks the excimer formed from two neighbouring building blocks pyrene. Alternatively, X may for example be phenanthroline, naphthalene, anthracene, tetracene, tetraphene, benzo[c]phenanthrene, triphenylene, chrysene, perylene, acenaphthene, biphenyl, fluorene, indole, acridine, phenazine, chinoline, bipyridine, phenanthridine, thianthrene, anthraquinone, phenoxathiine, fluorescein, flavine, coumarine, psoralen, purine, pyrimidine and derivatives thereof. Preferred building blocks X are phenanthrene, phenanthroline, chrysene, anthraquinone, purine, pyrimidine and derivatives thereof. Preferred combinations of pairs of building blocks P and building block X are pyrene/pyrene and phenanthrene; pyrene/pyrene and phenanthroline; and pyrene/pyrene and chrysene.

Linkers are chosen such as to allow incorporation of the aromatic or heteroaromatic building blocks P and X, respectively, into the backbone of the oligonucleotide, and at the same time define the proper distance from the backbone in order to provide good interaction with the corresponding duplex partner. A linker may consist of two linker groups as defined hereinafter, each linked on one end to two different positions in the aromatic or heteroaromatic system P and X, respectively, and, on the other end, to the sugar moiety of a nucleoside or nucleoside analogue through a phosphate group attached to the neighbouring sugar moiety, or to a phosphate group attached to a linker of a neighbouring aromatic or heteroaromatic system P and X, respectively. Alternatively, the linker may be a single group attached on one end to the aromatic or heteroaromatic system P and X, respectively, and having at the other end two connecting points to one or two nucleosides or nucleoside analogues of the backbone and/or to one or two neighbouring aromatic or heteroaromatic system P or X, respectively, through two phosphate groups linked to the neighbouring sugar moieties or linker of the neighbouring group P or X.

Preferred are two linker groups connected to P and X, respectively, as described hereinbefore and hereinafter.

The two linker groups may be the same or different, and are characterized by the following formula

    (I),

    (II), or

    (III)

wherein
A and B are bound to the aromatic or heteroaromatic system P or X;
A is —O—, —(C=Y)— or —W—(C=Y)—Z—;
B is a bond or —CH$_2$CH$_2$—W—(C=Y)—Z—;
D is 1,4-cyclohexylene;
V is O, NR or S;
W is CH$_2$, O, NH or S;
Y is O, NH, NR, H/OH, H/NH$_2$ or H/H;
Z is O, NR, (CH$_2$)$_q$ or a bond;
R is C$_1$-C$_4$-alkyl;
p is an integer from 1 to 10, preferably from 2 to 6; and
q is an integer from 1 and 6, preferably from 1 to 3;
and wherein one oxygen atom —O— is bound to a phosphate group attached to a neighbouring sugar moiety or a linker of a neighbouring aromatic or heteroaromatic system P or X.

A single linker group is likewise of formula

    (IV), or

    (V), wherein
A, B, V and p are defined as hereinbefore and E is —O—CH$_2$CH(—O—)CH$_2$— wherein the two oxygen atoms —O— are bound to two phosphate groups attached to neighbouring sugar moieties and/or a linker of a neighbouring aromatic or heteroaromatic system P or X.

The building blocks P and X are substantially different from the sugar derivatives of the natural nucleotides, and, together with the linker, they substitute for both essential components of natural nucleotides, i.e. the sugar-phosphate backbone and the nucleic acid base. The arrangement of the linkers and the aromatic or heteroaromatic moiety results in a building block P (in the "first sequence"), which prefers a similar building block X (in the "third sequence") in opposite position in a nucleic acid-like duplex P—X. If e.g. two phenanthrenes are arranged in this way, a stable duplex is formed. No significant destabilization is observed in comparison to an unmodified duplex containing a normal base pair (A-T or C-G) instead of the phenanthrenes. On the other hand, if a phenanthrene is placed opposite to a natural base (A, T, C or G), a significant destabilization is observed, much like in the case of a mismatch in the Watson/Crick base-pairing pattern.

Such interaction P-X stabilizes the stem of a molecular beacon. Depending on the number of aromatic or heteroaromatic systems P—X, the number of base pairs of nucleosides or also nucleoside analogues (i.e. the number n or m) in such a stem region may be kept small. For example, two duplex pairs of aromatic or heteroaromatic systems P—X reduce the number of required natural base pairs (A-T or C-G) in a molecular beacon stem to a small number, such as three. n is an integer from 1 to 10, preferably from 3 to 6, for example 3 or 4. m is likewise an integer from 1 to 10, preferably from 3 to 6, for example 3 or 4. n or m are usually the same integer, but may differ with the result that the additional nucleotide in the "first sequence" does not have a nucleobase in the "third sequence" for pairing, and vice versa.

To place such aromatic or heteroaromatic building blocks P and X according to the invention in the stem of a beacon is advantageous. They interact with each other in an interstrand stacking mode. This leads to a stable stem in the absence of a target polynucleotide. In the presence of a target polynucleotide, such as a target sequence within a DNA or RNA, the stem is opened and the duplex pairs P—X and natural base pairs present in the stem are "de-hybridised" or denatured. Since the aromatic or heteroaromatic building blocks P and X do not interact with natural nucleobases, there is little or no chance that they contribute to any mis-pairing with non-target polynucleotides. Such a behaviour is desirable: efficient and selective pairing in the stem of the (hairpin) molecular beacon in the absence of the target polynucleotide, and minimal interaction with any natural or unnatural base, which is not a neighbour in the backbone.

Two neighbouring building blocks P in the "first sequence" are able to form an excimer or exciplex on breaking the interaction between "first sequence" and "third sequence" following hybridisation of the "second sequence" with the target polynucleotide. If e.g. two pyrenes P are in close proximity, they form an excimer upon UV irradiation, which relaxes from the excited state by emission of a longer wave length radiation. This radiation can be used as a detection signal. Detection signals are essential parts of molecular beacons. Thus, by the use of neighbouring aromatic or heteroaromatic hydrocarbons P further sophisticated dyes and quenchers become obsolete and can be dismissed. This renders the composition of a molecular beacon according the invention substantially simpler than standard molecular beacons of the state of the art.

Figure 1:
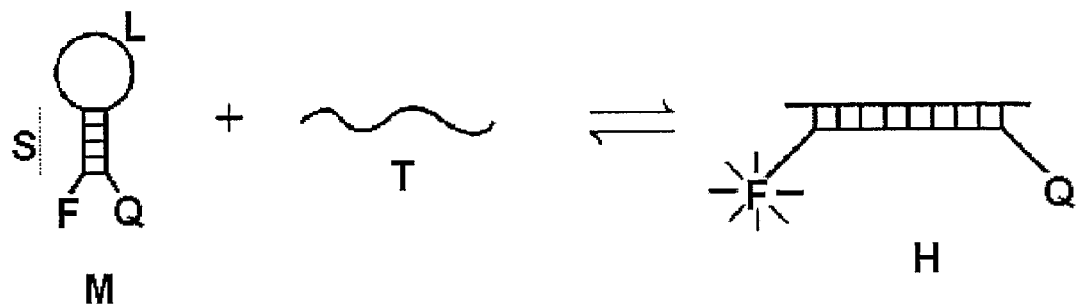
FIG. 1: Schematic representation of the reaction of a molecular beacon with a target polynucleotide according to the state of the art.
Figure 2:
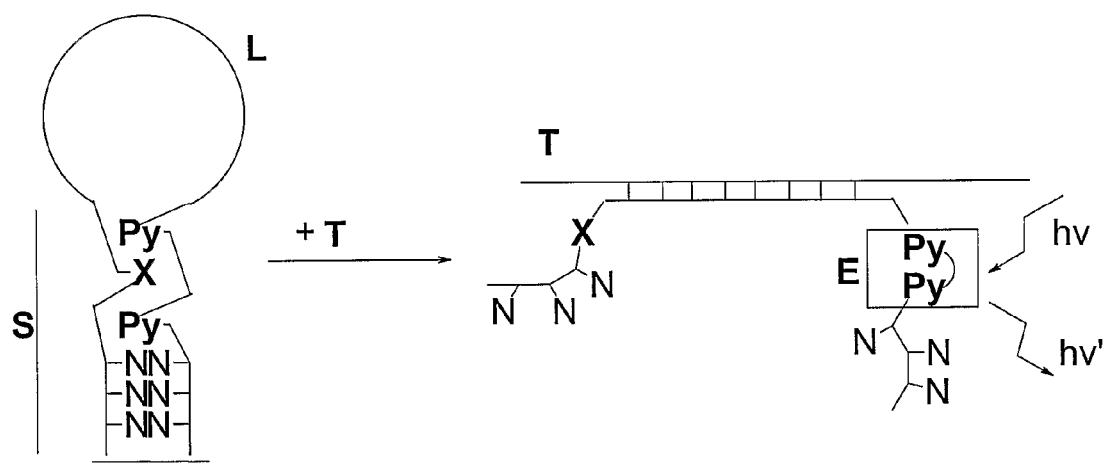
FIG. 2: Schematic representation of the reaction of a molecular beacon with a target polynucleotide according to the invention.

The combination of several non-nucleosidic aromatic or heteroaromatic building blocks P and X placed in juxtaposed and opposite position in the stem of a molecular beacon results in increased specificity and increased simplicity. One version of such a molecular beacon is shown in FIG. 2. In the absence of the target, the building block X, e.g. phenanthrene, prevents the formation of an excimer because it inserts itself between the two pyrenes (Py, corresponding to P). In the presence of the target, the loop region hybridises to the target, the stem is opened and, hence, the building block X is moved away form the two pyrenes P, which now form an excimer on irradiation. This has two effects: Firstly, the arms of the former stem are less likely to take part in any pairing interactions with other targets, since both X (e.g. phenanthrene) and Py (P) do not pair with natural nucleobases; secondly, the formation of an excimer can be used as a detection signal, which reveals the presence of the target sequence. It is possible to use more pyrene and/or phenanthrene building blocks in the stem than shown in FIG. 2, further reducing the number of natural base pairs (A-T and/or C-G) required for stable formation of the hairpin stem. Furthermore, the pyrene and/or phenanthrenes can be located anywhere in the stem, as long as they are arranged in a way to prevent excimer formation in the absence of the target and enable excimer formation in the presence of the target.

Whether a particular combination of a polyaromatic or heteroaromatic system and a linker is suitable as a component of a molecular beacon of the invention may be determined in melting temperature analyses of correspondingly modified duplexes. As an example, pyrenedicarboxamide, phenan threnedicarboxamide and phenanthrolinedicarboxamide with alkylene chain linkers of various length are tested in a standard oligonucleotide replacing an A-T pair (Tables 1-3). The same procedure can be applied to any of the mentioned polyaromatic or heteroaromatic systems and linkers described hereinbefore. Combinations of aromatic or heteroaromatic systems and linkers are chosen which give an increase of melting temperature or only a small decrease of melting temperature when compared to A-T or C-G-containing hybridising oligonucleotides.

The present invention provides molecular beacons with a characteristic fluorescence and very large Stokes shift (typically >100 nm).

The present invention differs clearly from the prior art as described e.g. in U.S. Pat. No. 5,925,517 (Tyagi, S. et al.) and related patents, in that the formation of the fluorophore (the excimer or exciplex) is structurally prevented by the building block X, e.g. by phenanthrene or other aromatic and heteroaromatic moieties as described above. The fluorophore consists of (at least) two structurally independent building blocks P, which have to be brought into close contact to be fluorescent. The detection of hybridisation is actually by a "light switch" consisting of generation vs. inhibition of the fluorophore formed by two or more building blocks P (excimer or exciplex).

The synthesis of oligonucleotides comprising aromatic or heteroaromatic building blocks P and X, respectively, follow standard methodology as exemplified for pyrene.

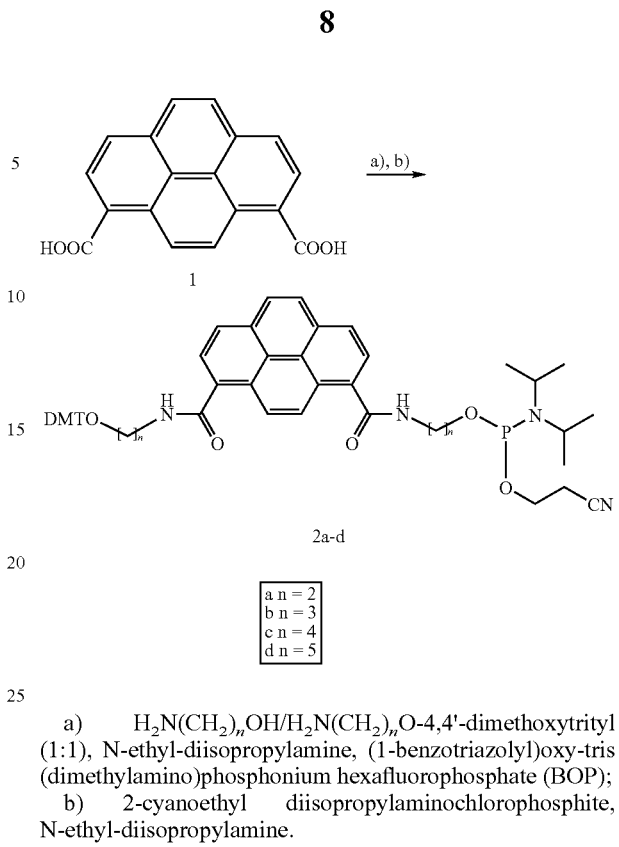

a) $H_2N(CH_2)_nOH/H_2N(CH_2)_nO$-4,4'-dimethoxytrityl (1:1), N-ethyl-diisopropylamine, (1-benzotriazolyl)oxy-tris(dimethylamino)phosphonium hexafluorophosphate (BOP);

b) 2-cyanoethyl diisopropylaminochlorophosphite, N-ethyl-diisopropylamine.

TABLE 1

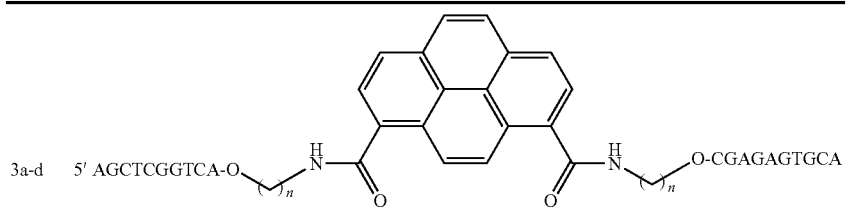

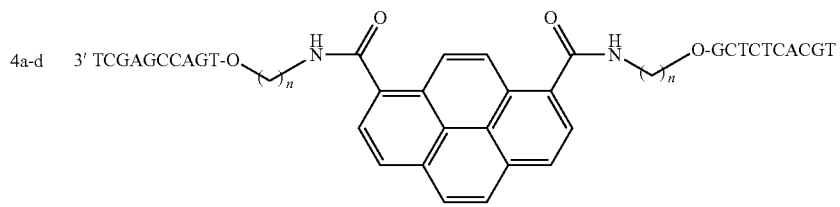

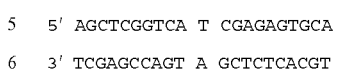

Tm values and fluorescence ratios of pyrene-modified DNA duplexes[a]

| duplex | 5*6 | 3a*4a | 3b*4b | 3c*4c | 3d*4d |
|---|---|---|---|---|---|
| Tm (° C.)[b] | 68.0 | 65.0 | 65.7 | 67.8 | 64.7 |
| ΔTm (° C.)[c] | — | −3.0 | −2.3 | −0.2 | −3.3 |
| excimer[d]/monomer[e] ratio | 0 | 1.68 | 2.58 | 3.24 | 0.48 |

[a]Conditions: oligomer concentration 1.0 μM, 1 mM Tris-HCl, 100 mM NaCl, pH 7.4; temperature gradient: 0.5° C./min.
[b]Melting temperatures Tm are determined from the maximum of the first derivative of the melting curve ($A_{260}$ against temperature); each Tm is the average of three independent experiments; experimental error: ±0.5° C.

TABLE 1-continued

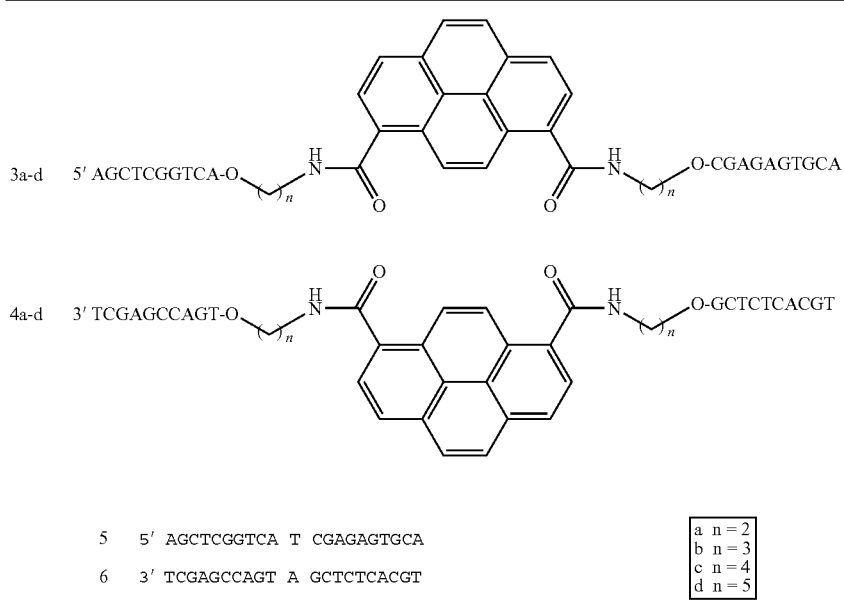

3a-d  5' AGCTCGGTCA-O-(CH2)n-NH-CO-[pyrene]-CO-NH-(CH2)n-O-CGAGAGTGCA 4a-d  3' TCGAGCCAGT-O-(CH2)n-NH-CO-[pyrene]-CO-NH-(CH2)n-O-GCTCTCACGT 5  5' AGCTCGGTCA T CGAGAGTGCA
6  3' TCGAGCCAGT A GCTCTCACGT a n = 2
b n = 3
c n = 4
d n = 5

Tm values and fluorescence ratios of pyrene-modified DNA duplexes[a]

| duplex | 5*6 | 3a*4a | 3b*4b | 3c*4c | 3d*4d |
|---|---|---|---|---|---|

[c]Difference in Tm relative to 5*6.

[d]493 nm;

[e]398 nm.

TABLE 2

Hybridisation data (Tm) of different phenanthrene containing oligonucleotides.
Conditions: oligomer concentration 1.5 µM, 10 mM Tris-HCl, 100 mM NaCl, pH 7.5.

| Oligo No. | Duplex | Tm (° C.) | ΔTm (° C.) | ΔTm/mod (° C.) |
|---|---|---|---|---|
| 7 | (5') AGC TCG GTC ATC GAG AGT GCA (SEQ ID No. 1) | 67.7 | | |
| 8 | (3') TCG AGC CAG TAG CTC TCA CGT (SEQ ID No. 2) | | | |
| 7 | (5') AGC TCG GTC ATC GAG AGT GCA (SEQ ID No. 1) | 64.0 | −3.7 | −3.7 |
| 9 | (3') TCG AGC CAG TP3G CTC TCA CGT (SEQ ID No. 3) | | | |
| 10 | (5') AGC TCG GTC AP3C GAG AGT GCA (SEQ ID No. 4) | 62.3 | −5.4 | −5.4 |
| 8 | (3') TCG AGC CAG TAG CTC TCA CGT (SEQ ID No. 2) | | | |
| 10 | (5') AGC TCG GTC AP3C GAG AGT GCA (SEQ ID No. 4) | 68.0 | 0.3 | 0.3 |
| 9 | (3') TCG AGC CAG TP3G CTC TCA CGT (SEQ ID No. 3) | | | |
| 11 | (5') AGC TCG GTC P3P3C GAG AGT GCA (SEQ ID No. 5) | 70.3 | 2.6 | 1.3 |
| 12 | (3') TCG AGC CAG P3P3G CTC TCA CGT (SEQ ID No. 6) | | | |
| 13 | (5') AGC TCG GTP3 AP3C GAG AGT GCA (SEQ ID No. 7) | 67.3 | −0.4 | −0.2 |
| 14 | (3') TCG AGC CAP3 TP3G CTC TCA CGT (SEQ ID No. 8) | | | |
| 15 | (5') AGC TCG GP3C AP3C GAG AGT GCA (SEQ ID No. 9) | 68.3 | 0.6 | 0.3 |
| 16 | (3') TCG AGC CP3G TP3G CTC TCA CGT (SEQ ID No. 10) | | | |

TABLE 2-continued

Hybridisation data (Tm) of different phenanthrene containing oligonucleotides.
Conditions: oligomer concentration 1.5 μM, 10 mM Tris-HCl, 100 mM NaCl, pH 7.5.

| Oligo No. | Duplex | Tm (° C.) | ΔTm (° C.) | ΔTm/mod (° C.) |
|---|---|---|---|---| oligo-P3-oligo =

TABLE 3

Influence of phenanthrene and phenanthroline nucleotide surrogates on the thermal stability of duplex DNA.

| Oligo No. | Duplex | Tm (° C.)$^{a,b}$ | ΔTm (° C.)$^c$ |
|---|---|---|---|
| 7 | (5') AGC TCG GTC ATC GAG AGT GCA (SEQ ID No. 1) | 68.0 | — |
| 8 | (3') TCG AGC CAG TAG CTC TCA CGT (SEQ ID No. 2) | | |
| 17 | (5') AGC TCG GTC AP2C GAG AGT GCA (SEQ ID No. 11) | 61.3 | −6.7 |
| 18 | (3') TCG AGC CAG TP2G CTC TCA CGT (SEQ ID No. 12) | | |
| 10 | (5') AGC TCG GTC AP3C GAG AGT GCA (SEQ ID No. 4) | 68.3 | 0.3 |
| 9 | (3') TCG AGC CAG TP3G CTC TCA CGT (SEQ ID No. 3) | | |
| 19 | (5') AGC TCG GTC AP4C GAG AGT GCA (SEQ ID No. 13) | 67.3 | −0.7 |
| 20 | (3') TCG AGC CAG TP4G CTC TCA CGT (SEQ ID No. 14) | | |
| 21 | (5') AGC TCG GTC AP5C GAG AGT GCA (SEQ ID No. 15) | 68.7 | 0.7 |
| 22 | (3') TCG AGC CAG TP5G CTC TCA CGT (SEQ ID No. 16) | | |
| 23 | (5') AGC TCG GTC AQ2C GAG AGT GCA (SEQ ID No. 17) | 65.6 | −2.4 |
| 24 | (3') TCG AGC CAG TQ2G CTC TCA CGT (SEQ ID No. 18) | | |
| 25 | (5') AGC TCG GTC AQ3C GAG AGT GCA (SEQ ID No. 19) | 71.1 | 3.1 |
| 26 | (3') TCG AGC CAG TQ3G CTC TCA CGT (SEQ ID No. 20) | | |
| 27 | (5') AGC TCG GTC AQ4C GAG AGT GCA (SEQ ID No. 21) | 70.6 | 2.6 |
| 28 | (3') TCG AGC CAG TQ4G CTC TCA CGT (SEQ ID No. 22) | | |
| 29 | (5') AGC TCG GTC AQ5C GAG AGT GCA (SEQ ID No. 23) | 70.2 | 2.2 |
| 30 | (3') TCG AGC CAG TQ5G CTC TCA CGT | | |

TABLE 3-continued

Influence of phenanthrene and phenanthroline nucleotide surrogates on the thermal stability of duplex DNA.

| Oligo No. | Duplex | Tm (° C.)$^{a,b}$ | ΔTm (° C.)$^{c}$ |
|---|---|---|---|

(SEQ ID No. 24)

Pn (phenanthrene)

Qn (phenanthroline)

P2,Q2: n = 2
P3,Q3: n = 3
P4,Q4: n = 4
P5,Q5: n = 5

$^{a}$Conditions: oligomer concentration 1.0 μM, 10 mM Tris-HCl, 100 mM NaCl, pH 7.4; temperature gradient: 0.5° C./min.
$^{b}$Melting temperatures (Tm) were determined from the maximum of the first derivative of the melting curve (A$_{260}$ against temperature); each Tm is the average of three independent experiments; experimental error: ±0.5° C.
$^{c}$Difference in Tm relative to the control duplex (7 + 8).

The invention further relates to a method for detecting the presence of a target polynucleotide comprising a specified nucleotide sequence, characterized in that the molecular beacon of the invention wherein the second sequence is able to hybridise to said specified nucleotide sequence is added to the target polynucleotide and the change in the fluorescence intensity is measured, and wherein an increase in fluorescence intensity due to excimer or exciplex formation is indicative of the presence of the target polynucleotide.

Reaction conditions are chosen depending on the length of the target oligonucleotide and the potential side reactions that may occur on hybridising with nucleotide sequences differing only slightly from the target sequence. Conditions are e.g. those described for what is normally applied in connection with Southern hybridisation, see e. g. Southern E.M., *J. Mol. Biol.* 1975, 98, 503-517. Such hybridisations are normally performed using solutions containing a hybridisation buffer, e.g. 20 mM Tris-HCl, 50 mM KCl and 5 mM MgCl$_2$, pH 8.0 (incubation for 15-60 min at 25 or 37° C.), followed by washing, e.g. as described by Sambrook et al., 1989, in "Molecular Cloning/A Laboratory Manual", Cold Spring Harbor).

The invention further concerns kits useful for the detection of a target polynucleotide, comprising a molecular beacon of the invention and optionally salt solutions, buffer solutions (either as ready solutions or as concentrated solutions to be diluted or as solids to be made up with water), directions for use and, optionally, hardware to perform the reactions, e.g. a thermostated bath, hybridisation chamber and the like. Salts provided are e.g. Li$^+$, Na$^+$, K$^+$, Mg$^{2+}$, Cl$^-$, HPO$_4^-$, PO$_4^{2-}$, NR$_4^+$, Tris, borate, spermine, and/or spermidine salts. Buffers considered are, e.g., tris ammonium EDTA, tris borate EDTA, phosphate, citrate, and/or acetate buffer.

EXAMPLES

Oligonucleotides are synthesized on a 392 DNA/RNA Synthesizer (Applied Biosystems) using standard phosphoramidite chemistry (S. L. Beaucage, M. H. Caruthers, *Tetrahedron Lett.* 1981, 22,1859-1862.; N. D. Sinha, J. Biernat, J. McManus, H. Koster, *Nucleic Acids Res.* 1984, 12, 4539-4557. The nucleoside phosphoramidites are from *CHEM-GENES* (Ashland, Mass.). The standard synthetic procedure (trityl-off mode) is used and, only for the non-natural phosphoramidites, the coupling time is extended to 5 min. After standard detachment and deprotection (conc. NH$_3$, 55° C., 16 h) the crude oligomers are purified by anion exchange HPLC (Machery-Nagel, Nucleogen DEAE 6017) and desalted over Sep-Pak cartridges (Waters, Milford, USA). All oligonucleotides are analysed by electrospray mass spectrometry. The masses are found to be within 0.0005% of the expected mass. UV melting curves are determined at 260 nm on a Varian Cary 3e spectrophotometer that is equipped with a Peltier block using the Varian WinUV software. Complementary oligonucleotides are mixed to 1:1 stoichiometry and the solutions adjusted to a final duplex concentration of 0.5-0.7 μM in 0.1 mM Tris-HCl, 100 mM NaCl, pH 7.5. A heating-cooling-heating cycle in the temperature range 0-90° or 20-90° C. is applied with a temperature gradient of 0.5° C./min. All ramps are indicating equilibrium melting processes. Tm values are defined as the maximum of the first derivative of the melting curve.

Synthesis of the Molecular Beacons

Phenanthrene and pyrene-derived phosphoramidite building blocks are incorporated into oligonucleotides via standard automated oligonucleotide synthesis using I$_2$/pyridine/water in the oxidation step. Coupling yields with the phenanthrene and pyrene building blocks are equal to the ones obtained with standard phosphoramidite building blocks. All oligonucleotides are purified by reverse phase HPLC and characterised by MS. Molecular weights of the molecular beacons (electrospray ionisation time-of-flight, ESI-TOF). Molecular Beacon 1: 8945.8 ([M-H]$^-$, calc. 8946.4). Molecular Beacon 2: 8327.6 ([M-H]$^-$, calc. 8328.0)

Procedure of Fluorescence Measurement

Molecular Beacon 1: 9.35 µl of an aqueous solution of molecular beacon 1 (214 µM) is mixed with 200 µl Tris-HCl (1 M, pH 7.4), 8 µl MgCl$_2$ (0.5 M) and 1782.6 µl, H$_2$O. Then the fluorescence is measured at room temperature. Excitation wavelength: 354 nm; excitation slit: 5 nm; emission slit: 7 nm. After that 23.9 µl, of the target polynucleotide (435 µM) is added to the mixture, and, after 5 min, the fluorescence is measured again. Excitation wavelength: 354 nm; excitation slit: 5 nm; emission slit: 7 nm.

Molecular Beacon 2: 15.44 µl of an aqueous solution of molecular beacon 2 (130 µM) is mixed with 200 µl Tris-HCl (1 M, pH 7.4), 8 µl MgCl$_2$ (0.5 M) and 1776.6 µl H$_2$O. Then the fluorescence is measured at room temperature. Excitation wavelength: 354 nm; excitation slit: 5 nm; emission slit: 7 nm. After that 23.9 µl of the target polynucleotide (435 µM) is added to the mixture, and, after 5 min, the fluorescence is measured again. Excitation wavelength: 354 nm; excitation slit: 5 nm; emission slit: 7 nm.

The invention claimed is:

1. A hairpin oligonucleotide or oligonucleotide analogue comprising:
   a first sequence consisting of n nucleotides and/or nucleotide analogues and two or more aromatic or heteroaromatic ring systems P linked to the oligonucleotide backbone and able to form an excimer or exciplex or exciplex, wherein at least two of the aromatic or heteroaromatic ring systems P are in neighboring positions;
   a second sequence consisting of an oligonucleotide probe able to hybridize with a target polynucleotide; and
   a third sequence consisting of m nucleotides and/or nucleotide analogues and one or more aromatic or heteroaromatic ring systems X linked to the oligonucleotide backbone, wherein said first and third sequence can form a stem of said hairpin oligonucleotide or oligonucleotide analogue and wherein at least one aromatic or heteroaromatic ring system X interacts with said at least two aromatic or heteroaromatic ring systems P of the first sequence when said stem is formed to inhibit excimer or exciplex formation.

2. The hairpin oligonucleotide or oligonucleotide analogue according to claim 1 wherein three or more consecutive nucleotides or nucleotide analogues of the first sequence form hydrogen bonds of the nucleobases to the same number of nucleotides or nucleotide analogues of the third sequence.

3. The hairpin oligonucleotide according to claim 1 wherein the nucleotide is desoxyribonucleic acid (DNA).

4. The hairpin oligonucleotide analogue according to claim 1 wherein the nucleotide analogues are PNA, HNA, LNA, TNA, homo-DNA, β-D-altropyranosyl nucleic acid, β-D-glucopyranosyl nucleic acid, β-D-allopyranosyl nucleic acid, RNA, 2'-OR-RNA, 2'-lyxopyranosyl nucleic acid, tricyclo-DNA, or bicyclo-DNA.

5. The hairpin oligonucleotide or oligonucleotide analogue according to claim 1 comprising two aromatic or heteroaromatic ring systems P and one or two aromatic or heteroaromatic ring systems X.

6. The hairpin oligonucleotide or oligonucleotide analogue according to claim 1 wherein the aromatic or heteroaromatic ring systems P and X are selected from the group consisting of phenanthrene, phenanthroline, naphthalene, anthracene, tetracene, tetraphene, benzo[c]phenanthrene, triphenylene, chrysene, perylene, acenaphthene, biphenyl, fluorene, indole, acridine, phenazine, chinoline, bipyridine, phenanthridine, thianthrene, anthraquinone, phenoxathiine, fluorescein, flavine, coumarine, psoralen, purine, pyrimidine, and derivatives thereof or phenyl or styryl extensions thereof.

7. The hairpin oligonucleotide or oligonucleotide analogue according to claim 1 wherein P is selected from the group consisting of pyrene, naphthalene, anthracene, tetracene, tetraphene, benzo[c]phenanthrene, triphenylene, perylene and derivatives thereof.

8. The hairpin oligonucleotide or oligonucleotide analogue according to claim 7 wherein P is pyrene.

9. The hairpin oligonucleotide or oligonucleotide analogue according to claim 1 wherein X is selected from the group consisting of phenanthrene, phenanthroline, naphthalene, anthracene, tetracene, tetraphene, benzo[c]phenanthrene, triphenylene, chrysene, perylene, acenaphthene, biphenyl, fluorene, indole, acridine, phenazine, chinoline, bipyridine, phenanthridine, thianthrene, anthraquinone, phenoxathiine, fluorescein, flavine, coumarine, psoralen, purine, pyrimidine and derivatives thereof.

10. The hairpin oligonucleotide or oligonucleotide analogue according to claim 9 wherein X is phenanthrene or phenanthroline.

11. The hairpin oligonucleotide or oligonucleotide analogue according to claim 9 wherein X is phenanthrene.

12. The hairpin oligonucleotide or oligonucleotide analogue according to claim 6, 7 or 9 wherein derivatives of aromatic or heteroaromatic ring systems P and X are those carrying substituents selected from alkyl, alkenyl, alkinyl, hydroxy, alkoxy, amino, carboxy, alkoxycarbonyl, carbamoyl, halogen, cyano, thio, alkylthio, sulfonyl, or nitro.

13. The hairpin oligonucleotide or oligonucleotide analogue according to claim 1 wherein pairs of building blocks P and building block X are selected from pyrene/pyrene and phenanthrene; pyrene/pyrene and phenanthroline; and pyrene/pyrene and chrysene.

14. The hairpin oligonucleotide or oligonucleotide analogue according to claim 1 wherein the aromatic or heteroaromatic ring systems P and X are linked to the oligonucleotide backbone through
   a) two linker groups of formula

   (I),

   (II), or

   (III)

wherein
   A and B are bound to the aromatic or heteroaromatic system P or X;
   A is —O—, —(C=Y)— or —W—(C=Y)—Z—;
   B is a bond or —CH$_2$CH$_2$—W—(C=Y)—Z—;
   D is 1,4-cyclohexylene;
   V is O, NR or S;
   W is CH$_2$, O, NH or S;
   Y is O, NH, NR, H/OH, H/NH$_2$ or H/H;
   Z is O, NR, (CH$_2$)$_q$ or a bond;
   R is C$_1$-C$_4$-alkyl;
   p is an integer from 1 to 10, preferably from 2 to 6; and
   q is an integer from 1 and 6, preferably from 1 to 3;
   and wherein one oxygen atom —O— is bound to a phosphate group attached to a neighbouring sugar moiety or a linker of a neighbouring aromatic or heteroaromatic system P or X; or
   b) a single linker group of formula

   (IV), or

   (V), wherein
   A is —O—, —(C=Y)— or —W—(C=Y)—Z—;
   B is a bond or —CH$_2$CH$_2$—W—(C=Y)—Z—;
   V is O, NR or S;
   W is CH$_2$, O, NH or S;
   Y is O, NH, NR, H/OH, H/NH$_2$ or H/H;
   Z is O, NR, (CH2)$_q$ or a bond;
   R is C$_1$-C$_4$-alkyl;
   p is an integer from 1 to 10, preferably from 2 to 6; and
   E is —O—CH$_2$CH(—O—)CH$_2$—;
   and wherein the two oxygen atoms —O— are bound to two phosphate groups attached to neighbouring sugar moieties and/or a linker of a neighbouring aromatic or heteroaromatic system P or X.

15. The hairpin oligonucleotide or oligonucleotide analogue according to claim 14 wherein the aromatic or heteroaromatic ring systems P and X are linked to the oligonucleotide backbone through two linker groups of formula —O—(CH$_2$)$_p$-A-     (I), wherein A is —W—(C=Y)—Z— and is bound to the aromatic or heteroaromatic system P or X through —Z—; W is NH; Y is O; Z is a bond;

p is an integer from 2 to 6;

and wherein the oxygen atom —O— is bound to a phosphate group attached to a neighbouring sugar moiety or a linker of a neighbouring aromatic or heteroaromatic system P or X.

16. A method for detecting the presence of a target polynucleotide comprising a specified nucleotide sequence, characterized in that a hairpin oligonucleotide or oligonucleotide analogue according to claim 1 wherein the second sequence is able to hybridise to said specified nucleotide sequence is added to the target polynucleotide and the change in the fluorescence intensity is measured, and wherein an increase in fluorescence intensity due to excimer or exciplex formation is indicative of the presence of the target polynucleotide.

17. A kit for detecting the presence of a target polynucleotide comprising a specified nucleotide sequence, comprising a hairpin oligonucleotide or oligonucleotide analogue according to claim 1, wherein the second sequence is able to hybridise to said specified nucleotide sequence, and salt and buffer solutions.

18. The hairpin oligonucleotide or oligonucleotide analogue according to claim 7 wherein P is perylene or a derivate thereof.

* * * * *

```
                        SEQUENCE LISTING

<160> NUMBER OF SEQ ID NOS: 24

<210> SEQ ID NO 1
<211> LENGTH: 21
<212> TYPE: DNA
<213> ORGANISM: Artificial
<220> FEATURE:
<223> OTHER INFORMATION: Synthetically generated DNA oligonucleotide

<400> SEQUENCE: 1
agctcggtca tcgagagtgc a                                              21

<210> SEQ ID NO 2
<211> LENGTH: 21
<212> TYPE: DNA
<213> ORGANISM: Artificial
<220> FEATURE:
<223> OTHER INFORMATION: Synthetically generated DNA oligonucleotide

<400> SEQUENCE: 2
tgcactctcg atgaccgagc t                                              21

<210> SEQ ID NO 3
<211> LENGTH: 20
<212> TYPE: DNA
<213> ORGANISM: Artificial
<220> FEATURE:
<223> OTHER INFORMATION: Synthetically generated DNA oligonucleotide
<220> FEATURE:
<221> NAME/KEY: misc_feature
<222> LOCATION: (10)..(11)
<223> OTHER INFORMATION: The nucleic acid between residues 10 and 11 is
      modified by a non-nucleosidic 3 carbon linker phenanthrene
      building block

<400> SEQUENCE: 3
tgcactctcg tgaccgagct                                                20

<210> SEQ ID NO 4
<211> LENGTH: 20
<212> TYPE: DNA
<213> ORGANISM: Artificial
<220> FEATURE:
<223> OTHER INFORMATION: Synthetically generated DNA oligonucleotides
<220> FEATURE:
<221> NAME/KEY: misc_feature
<222> LOCATION: (10)..(11)
<223> OTHER INFORMATION: The nucleic acid between residues 10 and 11 is
      modified by a non-nucleosidic 3 carbon linker phenanthrene
      building block

<400> SEQUENCE: 4
```
agctcggtca cgagagtgca                                             20

<210> SEQ ID NO 5
<211> LENGTH: 19
<212> TYPE: DNA
<213> ORGANISM: Artificial
<220> FEATURE:
<223> OTHER INFORMATION: Synthetically generated DNA oligonucleotides
<220> FEATURE:
<221> NAME/KEY: misc_feature
<222> LOCATION: (9)..(10)
<223> OTHER INFORMATION: The nucleic acid between residues 9 and 10 is
      modified by two non-nucleosidic 3 carbon linker phenanthrene
      building block

<400> SEQUENCE: 5
agctcggtcc gagagtgca                                              19

<210> SEQ ID NO 6
<211> LENGTH: 19
<212> TYPE: DNA
<213> ORGANISM: Artificial
<220> FEATURE:
<223> OTHER INFORMATION: Synthetically generated DNA oligonucleotides
<220> FEATURE:
<221> NAME/KEY: misc_feature
<222> LOCATION: (10)..(11)
<223> OTHER INFORMATION: The nucleic acid between residues 10 and 11 is
      modified by two non-nucleosidic 3 carbon linker phenanthrene
      building block

<400> SEQUENCE: 6
tgcactctcg gaccgagct                                              19

<210> SEQ ID NO 7
<211> LENGTH: 19
<212> TYPE: DNA
<213> ORGANISM: Artificial
<220> FEATURE:
<223> OTHER INFORMATION: Synthetically generated DNA oligonucleotides
<220> FEATURE:
<221> NAME/KEY: misc_feature
<222> LOCATION: (8)..(9)
<223> OTHER INFORMATION: The nucleic acid between residues 8 and 9 is
      modified by a non-nucleosidic 3 carbon linker phenanthrene
      building block
<220> FEATURE:
<221> NAME/KEY: misc_feature
<222> LOCATION: (9)..(10)
<223> OTHER INFORMATION: The nucleic acid between residues 9 and 10 is
      modified by a non-nucleosidic 3 carbon linker phenanthrene
      building block

<400> SEQUENCE: 7
agctcggtac gagagtgca                                              19

<210> SEQ ID NO 8
<211> LENGTH: 19
<212> TYPE: DNA
<213> ORGANISM: Artificial
<220> FEATURE:
<223> OTHER INFORMATION: Synthetically generated DNA oligonucleotides
<220> FEATURE:
<221> NAME/KEY: misc_feature
<222> LOCATION: (10)..(11)
<223> OTHER INFORMATION: The nucleic acid between residues 10 and 11 is
      modified by a non-nucleosidic 3 carbon linker phenanthrene
      building block
<220> FEATURE:
<221> NAME/KEY: misc_feature
<222> LOCATION: (11)..(12)

```
<223> OTHER INFORMATION: The nucleic acid between residues 11 and 12 is
      modified by a non-nucleosidic 3 carbon linker phenanthrene
      building block

<400> SEQUENCE: 8
tgcactctcg taccgagct                                                19

<210> SEQ ID NO 9
<211> LENGTH: 19
<212> TYPE: DNA
<213> ORGANISM: Artificial
<220> FEATURE:
<223> OTHER INFORMATION: Synthetically generated DNA oligonucleotides
<220> FEATURE:
<221> NAME/KEY: misc_feature
<222> LOCATION: (7)..(8)
<223> OTHER INFORMATION: The nucleic acid between residues 7 and 8 is
      modified by a non-nucleosidic 3 carbon linker phenanthrene
      building block
<220> FEATURE:
<221> NAME/KEY: misc_feature
<222> LOCATION: (9)..(10)
<223> OTHER INFORMATION: The nucleic acid between residues 9 and 10 is
      modified by a non-nucleosidic 3 carbon linker phenanthrene
      building block

<400> SEQUENCE: 9
agctcggcac gagagtgca                                                19

<210> SEQ ID NO 10
<211> LENGTH: 19
<212> TYPE: DNA
<213> ORGANISM: Artificial
<220> FEATURE:
<223> OTHER INFORMATION: Synthetically generated DNA oligonucleotides
<220> FEATURE:
<221> NAME/KEY: misc_feature
<222> LOCATION: (10)..(11)
<223> OTHER INFORMATION: The nucleic acid between residues 10 and 11 is
      modified by a non-nucleosidic 3 carbon linker phenanthrene
      building block
<220> FEATURE:
<221> NAME/KEY: misc_feature
<222> LOCATION: (12)..(13)
<223> OTHER INFORMATION: The nucleic acid between residues 12 and 13 is
      modified by a non-nucleosidic 3 carbon linker phenanthrene
      building block

<400> SEQUENCE: 10
tgcactctcg tgccgagct                                                19

<210> SEQ ID NO 11
<211> LENGTH: 20
<212> TYPE: DNA
<213> ORGANISM: Artificial
<220> FEATURE:
<223> OTHER INFORMATION: Synthetically generated DNA oligonucleotides
<220> FEATURE:
<221> NAME/KEY: misc_feature
<222> LOCATION: (10)..(11)
<223> OTHER INFORMATION: The nucleic acid between residues 10 and 11 is
      modified by a non-nucleosidic 2 carbon linker phenanthrene
      building block

<400> SEQUENCE: 11
agctcggtca cgagagtgca                                               20

<210> SEQ ID NO 12
<211> LENGTH: 20
<212> TYPE: DNA
<213> ORGANISM: Artificial
```

```
<220> FEATURE:
<223> OTHER INFORMATION: Synthetically generated DNA oligonucleotides
<220> FEATURE:
<221> NAME/KEY: misc_feature
<222> LOCATION: (10)..(11)
<223> OTHER INFORMATION: The nucleic acid between residues 10 and 11 is
      modified by a non-nucleosidic 2 carbon linker phenanthrene
      building block

<400> SEQUENCE: 12
tgcactctcg tgaccgagct                                                    20

<210> SEQ ID NO 13
<211> LENGTH: 20
<212> TYPE: DNA
<213> ORGANISM: Artificial
<220> FEATURE:
<223> OTHER INFORMATION: Synthetically generated DNA oligonucleotides
<220> FEATURE:
<221> NAME/KEY: misc_feature
<222> LOCATION: (10)..(11)
<223> OTHER INFORMATION: The nucleic acid between residues 10 and 11 is
      modified by a non-nucleosidic 4 carbon linker phenanthrene
      building block

<400> SEQUENCE: 13
agctcggtca cgagagtgca                                                    20

<210> SEQ ID NO 14
<211> LENGTH: 20
<212> TYPE: DNA
<213> ORGANISM: Artificial
<220> FEATURE:
<223> OTHER INFORMATION: Synthetically generated DNA oligonucleotides
<220> FEATURE:
<221> NAME/KEY: misc_feature
<222> LOCATION: (10)..(11)
<223> OTHER INFORMATION: The nucleic acid between residues 10 and 11 is
      modified by a non-nucleosidic 4 carbon linker phenanthrene
      building block

<400> SEQUENCE: 14
tgcactctcg tgaccgagct                                                    20

<210> SEQ ID NO 15
<211> LENGTH: 20
<212> TYPE: DNA
<213> ORGANISM: Artificial
<220> FEATURE:
<223> OTHER INFORMATION: Synthetically generated DNA oligonucleotides
<220> FEATURE:
<221> NAME/KEY: misc_feature
<222> LOCATION: (10)..(11)
<223> OTHER INFORMATION: The nucleic acid between residues 10 and 11 is
      modified by a non-nucleosidic 5 carbon linker phenanthrene
      building block

<400> SEQUENCE: 15
agctcggtca cgagagtgca                                                    20

<210> SEQ ID NO 16
<211> LENGTH: 20
<212> TYPE: DNA
<213> ORGANISM: Artificial
<220> FEATURE:
<223> OTHER INFORMATION: Synthetically generated DNA oligonucleotides
<220> FEATURE:
<221> NAME/KEY: misc_feature
<222> LOCATION: (10)..(11)
<223> OTHER INFORMATION: The nucleic acid between residues 10 and 11 is
      modified by a non-nucleosidic 5 carbon linker phenanthrene
``` building block

<400> SEQUENCE: 16
tgcactctcg tgaccgagct                                                     20

<210> SEQ ID NO 17
<211> LENGTH: 20
<212> TYPE: DNA
<213> ORGANISM: Artificial
<220> FEATURE:
<223> OTHER INFORMATION: Synthetically generated DNA oligonucleotides
<220> FEATURE:
<221> NAME/KEY: misc_feature
<222> LOCATION: (10)..(11)
<223> OTHER INFORMATION: The nucleic acid between residues 10 and 11 is
      modified by a non-nucleosidic 2 carbon linker phenanthroline
      building block

<400> SEQUENCE: 17
agctcggtca cgagagtgca                                                     20

<210> SEQ ID NO 18
<211> LENGTH: 20
<212> TYPE: DNA
<213> ORGANISM: Artificial
<220> FEATURE:
<223> OTHER INFORMATION: Synthetically generated DNA oligonucleotides
<220> FEATURE:
<221> NAME/KEY: misc_feature
<222> LOCATION: (10)..(11)
<223> OTHER INFORMATION: The nucleic acid between residues 10 and 11 is
      modified by a non-nucleosidic 2 carbon linker phenanthroline
      building block

<400> SEQUENCE: 18
tgcactctcg tgaccgagct                                                     20

<210> SEQ ID NO 19
<211> LENGTH: 20
<212> TYPE: DNA
<213> ORGANISM: Artificial
<220> FEATURE:
<223> OTHER INFORMATION: Synthetically generated DNA oligonucleotides
<220> FEATURE:
<221> NAME/KEY: misc_feature
<222> LOCATION: (10)..(11)
<223> OTHER INFORMATION: The nucleic acid between residues 10 and 11 is
      modified by a non-nucleosidic 3 carbon linker phenanthroline
      building block

<400> SEQUENCE: 19
agctcggtca cgagagtgca                                                     20

<210> SEQ ID NO 20
<211> LENGTH: 20
<212> TYPE: DNA
<213> ORGANISM: Artificial
<220> FEATURE:
<223> OTHER INFORMATION: Synthetically generated DNA oligonucleotides
<220> FEATURE:
<221> NAME/KEY: misc_feature
<222> LOCATION: (10)..(11)
<223> OTHER INFORMATION: The nucleic acid between residues 10 and 11 is
      modified by a non-nucleosidic 3 carbon linker phenanthroline
      building block

<400> SEQUENCE: 20
tgcactctcg tgaccgagct                                                     20

```
<210> SEQ ID NO 21
<211> LENGTH: 20
<212> TYPE: DNA
<213> ORGANISM: Artificial
<220> FEATURE:
<223> OTHER INFORMATION: Synthetically generated DNA oligonucleotides
<220> FEATURE:
<221> NAME/KEY: misc_feature
<222> LOCATION: (10)..(11)
<223> OTHER INFORMATION: The nucleic acid between residues 10 and 11 is
      modified by a non-nucleosidic 4 carbon linker phenanthroline
      building block

<400> SEQUENCE: 21
agctcggtca cgagagtgca                                             20

<210> SEQ ID NO 22
<211> LENGTH: 20
<212> TYPE: DNA
<213> ORGANISM: Artificial
<220> FEATURE:
<223> OTHER INFORMATION: Synthetically generated DNA oligonucleotides
<220> FEATURE:
<221> NAME/KEY: misc_feature
<222> LOCATION: (10)..(11)
<223> OTHER INFORMATION: The nucleic acid between residues 10 and 11 is
      modified by a non-nucleosidic 4 carbon linker phenanthroline
      building block

<400> SEQUENCE: 22
tgcactctcg tgaccgagct                                             20

<210> SEQ ID NO 23
<211> LENGTH: 20
<212> TYPE: DNA
<213> ORGANISM: Artificial
<220> FEATURE:
<223> OTHER INFORMATION: Synthetically generated DNA oligonucleotides
<220> FEATURE:
<221> NAME/KEY: misc_feature
<222> LOCATION: (10)..(11)
<223> OTHER INFORMATION: The nucleic acid between residues 10 and 11 is
      modified by a non-nucleosidic 5 carbon linker phenanthroline
      building block

<400> SEQUENCE: 23
agctcggtca cgagagtgca                                             20

<210> SEQ ID NO 24
<211> LENGTH: 20
<212> TYPE: DNA
<213> ORGANISM: Artificial
<220> FEATURE:
<223> OTHER INFORMATION: Synthetically generated DNA oligonucleotides
<220> FEATURE:
<221> NAME/KEY: misc_feature
<222> LOCATION: (10)..(11)
<223> OTHER INFORMATION: The nucleic acid between residues 10 and 11 is
      modified by a non-nucleosidic 5 carbon linker phenanthroline
      building block

<400> SEQUENCE: 24
tgcactctcg tgaccgagct                                             20
```